United States Patent [19]

LeVeen et al.

[11] 4,346,706
[45] Aug. 31, 1982

[54] PARENTERAL ADMINISTRATION OF NUTRIMENTS

[76] Inventors: Harry H. LeVeen, 800 Poly Pl., Brooklyn, N.Y. 11220; Vincent A. Piccone, 377 Gansevoort Blvd., Staten Island, N.Y. 10314

[21] Appl. No.: 239,474

[22] Filed: Mar. 2, 1981

Related U.S. Application Data

[63] Continuation of Ser. No. 25,374, Mar. 30, 1979, abandoned.

[51] Int. Cl.$^3$ .............................................. A61M 5/00
[52] U.S. Cl. .............................................. 128/214 R
[58] Field of Search ........... 128/213 R, 214 R, 214 A, 128/214 B, 214 C, 214 D, 214 E, 214 F, 349 R

[56] References Cited

PUBLICATIONS

Brown et al., Advances in Experimental Biology & Medicine, vol. 37B, pp. 1103–1108, Plenum Press, N.Y., London.

Harris et al., Jour. of Pediatrics, vol. 82, No. 6, pp. 929–939.

Piccone et al., Surgery, vol. 63, No. 1, pp. 29–37, Jan. 1968.

Piccone et al., Am. Jour. of Surg., vol. 115, No. 1, pp. 17–21, Jan. 1968.

Sabiston, Textbook of Surgery, 10th Ed. pp. 165–169, 1003, 1020, W. B. Saunders Co. (PTO 7-1973).

Fatt, I., Polarographic Oxygen Sensor, CRC Press, Cleveland, Ohio, 1976.

Primary Examiner—C. Fred Rosenbaum
Attorney, Agent, or Firm—Brooks, Haidt, Haffner & Delahunty

[57] ABSTRACT

Novel methods for the parenteral administration of nutriments to patients, which comprises opening the umbilical vein and introducing an aqueous solution of nutriments into the opened vein, thereby permitting the maintenance of patients who are unable to ingest sufficient foods by the normal oral route.

6 Claims, No Drawings

PARENTERAL ADMINISTRATION OF NUTRIMENTS

This application is a continuation of application Ser. No. 025,374, field Mar. 30, 1979 and now abandoned.

BACKGROUND OF THE INVENTION

The present invention relates to the parenteral administration of nutriments to individuals, and more particularly, it relates to novel methods for the intravenous administration of hyperalimentary solutions to individuals who are unable to ingest sufficient materials to sustain themselves because of medical complications.

In the practice of medicine, patients are encountered who are malnourished and who cannot ingest any food orally, or who are unable to ingest sufficient quantities of food to sustain themselves. Such a condition is especially found in patients who have diseases of the alimentary system which, for example, interfere with the stomach or intestines. Similarly, difficulties in fulfilling the nutritional requirements of patients undergoing procedures such as esophageal resection are frequently encountered.

Attempts have been made to restore such patients nutritionally by intravenous hyperalimentation. Such intravenous hyperalimentation employs aqueous intravenous fluids having high concentrations of glucose and amino acids, fat and/or minerals which are injected into the peripheral vascular system. High concentrations of the nutrients are required in order to avoid the need for infusion of excessive quantities of fluids. Unfortunately, the high concentrations required are hyperosmolar and accordingly cause injury to the vessel wall and necessitate the placement of a catheter into a large systemic vein, such as the subclavian, or into the superior vena cava. Naturally, this puts a considerable load on the vascular system, because nutrients are normally absorbed from the intestinal tract and pass through the body organs so that there is no circulation of hyperosmolar glucose and amino acids. It has been found with intravenous hyperalimentation conducted conventionally that osmolar dehydration and hyperosmotic coma can occur. In some cases, metabolic acidosis occurs, and this can be a fatal complication. Further, rebound hyperinsulinemia can be a life-threatening event, so that prevention of these complications requires continued aggressive surveillance of the blood and urine glucose levels.

Other problems also occur in intravenous hyperalimentation. These arise from alterations in the peripheral blood amino acid concentration and composition. Thus, the amino acids can reach the cerebral circulation and cause alteration of the cerebral function. For instance, tryptophane, an essential amino acid, is required to be infused, but if it reaches the brain in high concentrations, it alters the serotonin concentration in the brain cells because tryptophane is a precursor of serotonin. Similarly, phenylalanine, another essential amino acid, causes excessive synthesis of norepinephrine and other catecholamines in the cerebral cells. The consequence of this systemic injection of amino acids can include such serious symptoms as muscle twitching and coma.

During fetal development, the umbilical vein returns blood from the placenta to the fetus. It was commonly assumed that, after division of the umbilical cord at birth, the lumen of the umbilical vein became obliterated and the vein wall then fibrosed. A cord-like remnant then persisted as the ligamentum teres hepatis in the free edge of the falciform ligament. In 1959, Gonzalez-Carbalhaes, *Rev. Sanid, Milit.* 12, 42 (1959), demonstrated that this "obliterated" vein could, in fact, be reopened to provide direct entry into the left portal vein. Since then, the reopened umbilical vein has been used for portography and chemotherapeutic purposes, as in the treatment of metastatic hepatic carcinomas. Various clinical and research uses of the reopened adult umbilical vein are described by Piccone, Bonanno, and LeVeen in *Surgery*, 63 (1), 29 (Jan. 1968).

THE INVENTION

It has now been found that it is possible to infuse hyperalimentary solutions intravenously and yet avoid the numerous difficulties which have arisen in prior art treatments. This invention accordingly provides an easily utilized and readily monitored avenue for sustaining the metabolic functions of patients who are unable to ingest nutriments normally via the oral route. Briefly, the present invention provides a method for parenteral administration of nutriments, which method comprises opening the umbilical vein and thereafter introducing into the vein an aqueous solution of nutriments.

Opening of the umbilical vein has already been demonstrated by Gonzalez-Carbalhaes, as mentioned above. In one technique, the collapsed umbilical vein is exposed after local anesthesia with a 2% aqueous lidocaine local anesthetic solution, and a short supraumbilical midline incision is carried down through the linea alba to the preperitoneal fat. The solid cord is isolated and hemisected. The collapsed lumen is then gently urged open with a hemostat.

Then, the smallest available Bakes dilator is advanced slowly and carefully into the lumen so as to avoid perforation. Firm resistance is generally encountered just proximal to the entrance to the left portal vein. A sudden "give" is encountered as the dilator passes this area of resistance and enters the portal vein. Thereafter, progressively larger dilators are introduced until the lumen accommodates a No. 16 to a No. 18 catheter.

In another technique, a specially pre-shaped, pliable, round-tipped catheter is gently advanced through the reopened umbilical vein until portal blood spontaneously flows back through the catheter. During the passage of the catheter through the umbilical vein, a plastic trochar keeps the curved tip straight. After introduction of the catheter into the left edge of the portal vein, the trochar is withdrawn and the catheter is returned to its pre-shaped curve so that it can be guided into the main portal vein. The catheter positioning is desirably checked angiographically before commencing any infusion of the aqueous hyperalimentation solutions.

One of the possible difficulties in carrying out the present method is the possibility of sepsis at the site where the catheter enters the body. In practice, it has been found that daily applications of an antiseptic such as Betadine solution to the skin surrounding the catheter entry site minimize the possibility of ascending infection along the catheter tract.

Administration of high caloric and high amino acid content aqueous solutions into the portal vein via the reopened umbilical vein, according to the present invention, takes advantage of the controlling influence of the liver biologically to modify the infusate before the passage of this material into the general circulatory system. It has been found that this avoids the aforementioned usual complications of hyperalimentation due to the high circulating levels of glucose and the nonphysiologic mixtures of amino acids. The prehepatic delivery of concentrated parenteral nutrients according to the present invention preserves the normal milieu of the systemic blood.

It has been found in studies carried out in connection with the present invention, utilizing indirect calorimetry with a Tissot gasometer, that the positive caloric balance which is obtained during the period of infusion is confirmed. These measurements are made by collecting expired air and determining the carbon dioxide content thereof and collecting the urine and noting the net positive balance of both calories and proteins.

It has been further found that umbilical vein infusion of high concentrations of glucose does not raise the systemic glucose levels, even though the administration of nutriments according to the present invention is continued for periods as long as six weeks. Further, metabolic acidosis is not found to occur. There has been no finding of glycosuria, and patients supplied nutriments according to this regimen actually gained weight.

The usual hazard of infections occurring with prior art systemic hyperalimentation did not occur with umbilical vein hyperalimentation according to the present invention. Amino acid analyses of peripheral blood have failed to reveal abnormal distribution patterns.

The ability of the liver to clear portal blood glucose and thereby regulate glucose homeostasis in the peripheral blood was studied by comparing the biochemical alterations of peripheral blood resulting from rapid infusion of concentrated glucose into a large central vein and later into the portal vein. Two hundred milliliters of a 25% glucose solution is infused during 20 minutes through the umbilical catheter about three weeks after surgery and then the same solution is infused at the same rate through a large central vein on the following day. Measures of peripheral blood and urine glucose levels and osmolarity are made before the start of the infusions and at hourly intervals for six hours after the 20-minute infusion. The glucose was measured by the automated glucose oxidase technique shown by Gochman et al., *Clin. Chem.* 18, 943. Osmolarity is determined from freezing point depression.

The long-term use of transumbilical hyperalimentation in ten patients having carcinoma of the esophagus has been studied. These patients have undergone esophago-gastrectomy and esophagogastrostomy. Hyperalimentation in these patients was indicated as desirable because of a marked pre-operative weight loss secondary to either dysphagia or obstruction and to poor toleration of food for two weeks following the vagotomy, which was attendant upon the esophageal resection.

With these patients, hyperalimentation according to the present invention was commenced on the first post-operative day and continued for the next 30 days. A hyperalimentation solution comprising 3 L of half Amigen amino acid solution and half 50% aqueous glucose was infused by the gravity drip method during the entire 24-hour period. Heparin was added to prevent portal vein thrombosis, and potassium supplements were added when appropriate. During the course of treatment, 500 mcg of Viatmin B-12 and 5 mg of folate were administered weekly. The Amigen contains magnesium phosphate and calcium.

During the course of this treatment, serum electrolytes, glucose, osmolarity, body temperature, and weight are measured daily. Urine specimens are collected over 24 hours and sampled for glucose concentration and osmolarity. Transumbilical angiograms are performed weekly in order to detect thrombosis in the portal vein.

Liver function is checked once a week. The post-operative radio nucleotide liver scan is compared with the pre-operative scan at the completion of the hyperalimentation. Indirect calorimetry and urinary nitrogen determinations are used to calculate the respiratory quotient and to estimate endogenous protein breakdown two or three weeks post-operatively during one day of hyperalimentation. Urinary nitrogen content is determined by a modification of the micro-Kjeldahl method. Further, the tips of the portal vein catheters are cultured at the time of removal.

The following Examples are given to illustrate embodiments of the invention as it is presently preferred to practice it. It will be understood that these Examples are illustrative, and the invention is not to be considered as restricted thereto except as indicated in the appended Claims.

The nutrient infusion utilized in the following Examples contains lipids, amino acid mixtures (fibrin hydrolysates prepared by hydrolysis and crystalline amino acid solutions), glucose and amino acid mixtures, and glucose solutions. The amino acid solutions are mixed equally with 50% glucose producing a 25% glucose and amino acid mixture. Each day, 3000 ml of the mixture is infused in the patient to supply 700 calories and 7.5 g of nitrogen for each 1000 cc. The mixture provides essential amino acids as follows: 400 mg lysine, 50 mg tryptophane, 100 mg phenylalanine, 100 mg methionine, 232 mg threonine, 636 mg leucine, 218 mg isoleucine, and 163 mg valine. In addition, 290 mg arginine, 116 mg histidine, 30 mg cysteine, 110 mg tyrosine, and glutamic acid are also included.

EXAMPLES I-IV

| | AVERAGE KILOCALORIES/HOUR | | | | |
|---|---|---|---|---|---|
| Example | Protein | Fat | Carbohydrate | Utilized Total | Infused Total |
| I | 7.01 | 1.89 | 55.01 | 63.91 | 260.00 |
| II | 18.15 | 14.17 | 43.50 | 75.82 | 94.58 |
| III | 11.01 | 5.02 | 54.55 | 70.58 | 157.00 |
| IV | 15.33 | 0 | 71.60 | 86.93 | 41.08 |

Rapid infusion of a concentrated glucose load into the portal vein via the reopened umbilical vein resulted in consistently lower serum glucose levels and less glycosuria than similar glucose loads infused at a similar rate into a systemic vein. The comparative effect of transumbilical infusions and systemic infusions of concentrated glucose solutions are within the usual range. No sugar was spilled into the urine, and reactive hypoglycemia was not encountered upon abrupt termination of hyperalimentation according to the present invention. The patients lost no weight post-operatively, and this compares with an average 15-pound weight loss in patients who were not treated according to the present invention after esophageal resection.

Indirect calorimetry in the patients receiving transportal hyperalimentation demonstrates positive caloric balance during the infusion period. In general, the mean calories infused were 259 cal/hr and the calories utilized were 62 cal/hr. Parenteral hyperalimentation via the transumbilical route resulted in respiratory quotient changes consistent with metabolic utilization of sugar and was sparing of protein. Weekly transumbilical portography shows no evidence of portal vein thrombosis and culture of catheters shows no growth of pathogens, even after one month. None of the patients developed sepsis, and there was not anastomotic breakdown. Moreover, the patients are more active and stronger post-operatively than patients not so treated.

It will also be understood by those skilled in the art that the techniques of the present invention can be used in conjunction with the infusion of other materials, such as antibiotics and medicines together with the alimentary fluids.

What is claimed is:

1. A method for parental administration of nutriments which comprises opening the umbilical vein and thereafter introducing into the vein an aqueous hyperalimentary solution of nutriments.

2. A method according to claim 1 wherein the aqueous solution is introduced by means of a catheter.

3. A method according to claim 2 wherein the tip of the catheter is introduced into the portal vein.

4. A method according to claim 1 wherein the nutriments include glucose and the essential amino acids.

5. A method according to claim 1 wherein the caloric content of the nutriments is at least equal to the daily caloric requirement.

6. A method according to claim 1 wherein the nutriments include at least the recommended daily allowance of amino acids, fat, carbohydrates, vitamins, and minerals.

* * * * *